(12) United States Patent
Jang et al.

(10) Patent No.: US 11,579,765 B2
(45) Date of Patent: Feb. 14, 2023

(54) DEVICE AND METHOD FOR SHARING OLFACTORY DATA BETWEEN REAL WORLD AND ONLINE WORLD

(71) Applicant: Daegu Gyeongbuk Institute of Science and Technology, Daegu (KR)

(72) Inventors: Jae Eun Jang, Daegu (KR); Hyuk Jun Kwon, Daegu (KR); Che Il Moon, Daegu (KR); Kyung In Jang, Icheon (KR); Ji Hwan Choi, Daegu (KR); Han Kyoung Choe, Daegu (KR); Su Jin Heo, Pohang-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 509 days.

(21) Appl. No.: 16/735,837

(22) Filed: Jan. 7, 2020

(65) Prior Publication Data

US 2020/0218415 A1    Jul. 9, 2020

(30) Foreign Application Priority Data

Jan. 8, 2019 (KR) .................. 10-2019-0002395

(51) Int. Cl.
  *G08B 21/00* (2006.01)
  *G06F 3/0487* (2013.01)
  *G06N 20/00* (2019.01)
  *G01N 33/00* (2006.01)

(52) U.S. Cl.
  CPC ....... *G06F 3/0487* (2013.01); *G01N 33/0001* (2013.01); *G01N 33/0031* (2013.01); *G06N 20/00* (2019.01)

(58) Field of Classification Search
  CPC .............. G06F 3/0487; G01N 33/0001; G01N 33/0031; G06N 20/00; G06N 3/08; G06Q 30/0629; G06Q 30/0631
  USPC ...................................................... 340/573.1
  See application file for complete search history.

(56) References Cited

U.S. PATENT DOCUMENTS

| | | | |
|---|---|---|---|
| 2014/0012794 A1* | 1/2014 | Dillon ..................... | G06N 5/04 706/46 |
| 2015/0051842 A1* | 2/2015 | Haddad .............. | G01N 33/0073 702/22 |
| 2016/0091470 A1* | 3/2016 | Gafsou .............. | G01N 33/0034 73/23.34 |

(Continued)

FOREIGN PATENT DOCUMENTS

| JP | 2003-290179 A | 10/2003 |
|---|---|---|
| JP | 2003290179 A | * 10/2003 |
| KR | 10-2018-0062011 | 6/2018 |

OTHER PUBLICATIONS

Korean Office Action dated Jul. 30, 2020, in connection with the Korean Patent Application No. 10-2019-0002395.

*Primary Examiner* — Mark S Rushing
(74) *Attorney, Agent, or Firm* — Hauptman Ham, LLP (57) ABSTRACT

Provided is an olfactory data sharing terminal including a receiver configured to receive olfactory data obtained by sensing an odor of an object through an olfactory sensor; a preference determiner configured to determine whether a user prefers the received olfactory data, based on a user olfactory function $f_{user}(x)$; and a display displaying a user preference for the received olfactory data.

11 Claims, 5 Drawing Sheets

(56) References Cited

U.S. PATENT DOCUMENTS

2017/0290541 A1* 10/2017 Albers ................. A61B 5/4082
2019/0021645 A1* 1/2019 Mochizuki ............. A61B 5/742

* cited by examiner

DEVICE AND METHOD FOR SHARING OLFACTORY DATA BETWEEN REAL WORLD AND ONLINE WORLD

CROSS-REFERENCE TO RELATED APPLICATION

This application claims the benefit of Korean Patent Application No. 10-2019-0002395, filed on Jan. 8, 2019, in the Korean Intellectual Property Office, the disclosure of which is incorporated herein in its entirety by reference.

BACKGROUND

1. Field

One or more embodiments relate to a method, a terminal, and a system for sharing olfactory data, and more particularly, to a method for enabling a user to indirectly recognize his or her olfactory preferences by using olfactory data of an object provided online without actually testing the object with regard to its olfactory properties.

2. Description of Related Art

Efforts to apply the five human senses of sight, hearing, smell, taste, and touch to machines have been made for a long time, and as a result, various technologies for sensors related to these senses have been introduced and developed.

PRIOR ART DOCUMENTS

Patent Documents

KR 2018-0062011

SUMMARY

One or more embodiments provide a method of recognizing an olfactory taste or olfactory preferences of an individual by using an olfactory sensor and sharing olfactory data between the real world and the online world.

Additional aspects will be set forth in part in the description which follows and, in part, will be apparent from the description, or may be learned by practice of the presented embodiments of the disclosure.

According to one or more embodiments, a method of sharing olfactory data between the real world and the online world, the method includes generating a user olfactory function $f_{user}(x)$ indicating a user preference for the odor of each of a plurality of objects through cumulative machine-learning for each of a plurality of users by using olfactory data obtained by sensing standard fragrance samples as input values and user preference test results for the standard fragrance samples as output values; receiving olfactory data obtained by sensing the odor of an object by using same olfactory sensor as used to sense the odor of the standard fragrance samples; determining user preferences by applying the received olfactory data to the user olfactory function $f_{user}(x)$; and displaying the determined user preferences.

According to one or more embodiments, the olfactory data includes at least one of gas chromatography information for analyzing gas ingredients generated from an odor of an object, information regarding chemical ingredients constituting the object, information regarding absorption and desorption between odor molecules and polymer elements, which may be extracted from the olfactory data, and sensing information sensed by each of a plurality of sensors constituting the olfactory sensor.

According to one or more embodiments, the user olfactory function $f_{user}(x)$ is generated by machine-learning with respect to at least one of information regarding protein components, chemical compositions, a composition ratio, and adsorption and desorption between odor molecules and polymer elements constituting the odor of an object preferred by each user.

According to one or more embodiments, in the determining of the user preferences, the olfactory data received by a receiver is matched with an olfactory data value sensed from a pre-stored standard fragrance sample that is most similar to the olfactory data, and the olfactory data value is input as an x value in the olfactory function $f_{user}(x)$ to determine a user preference.

According to one or more embodiments, in the determining of the user preferences, a user preference for each variable constituting the olfactory data received by a receiver according to the lapse of time is determined based on a result value of the olfactory function $f_{user}(x)$ that is machine-trained for each variable constituting the olfactory data.

According to one or more embodiments, a display unit displays a user preference with respect to the odor of the object according to the lapse of time.

According to one or more embodiments, an olfactory data sharing system for recognizing an olfactory preference through a second terminal through communication between a first terminal and the second terminal, the olfactory data sharing system includes the first terminal configured to provide olfactory data obtained by sensing an odor of an object by using an olfactory sensor; and the second terminal configured to receive the olfactory data, determine whether a user prefers the olfactory data based on a user olfactory function fuser(x), and display a user preference for the olfactory data.

According to one or more embodiments, the olfactory data sharing system further includes a user preference manager configured to store the olfactory function fuser(x) for each of a plurality of users, and manage a user preference for the olfactory data for each user based on the olfactory function $f_{user}(x)$ stored for each user.

According to one or more embodiments, the first terminal is further configured to predict a user preference for olfactory data obtained by sensing an odor of an arbitrary object, based on the olfactory function $f_{user}(x)$ for each user stored in the user preference manager.

According to one or more embodiments, an olfactory data sharing terminal includes an olfactory data provider configured to provide olfactory data obtained by sensing an odor of an object through an olfactory sensor; and a user preference manager configured to store an olfactory function fuser(x) for each of a plurality of users, and manage a user preference fo According to one or more embodiments, an olfactory data sharing terminal includes a user olfactory function learner configured to generate a user olfactory function fuser(x) indicating user preference for the odor of each of a plurality of objects through cumulative machine-learning for each of a plurality of users by using olfactory data obtained by sensing standard fragrance samples as input values and user preference test results for the standard fragrance samples as output values; a receiver configured to receive olfactory data obtained by sensing the odor of an object by using same olfactory sensor as used to sense the odor of the standard fragrance samples; a user preference determiner configured to determine user preferences by applying the received olfactory data to the user olfactory function fuser(x); and a display unit configured to display the determined user preferences.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Figure 1:
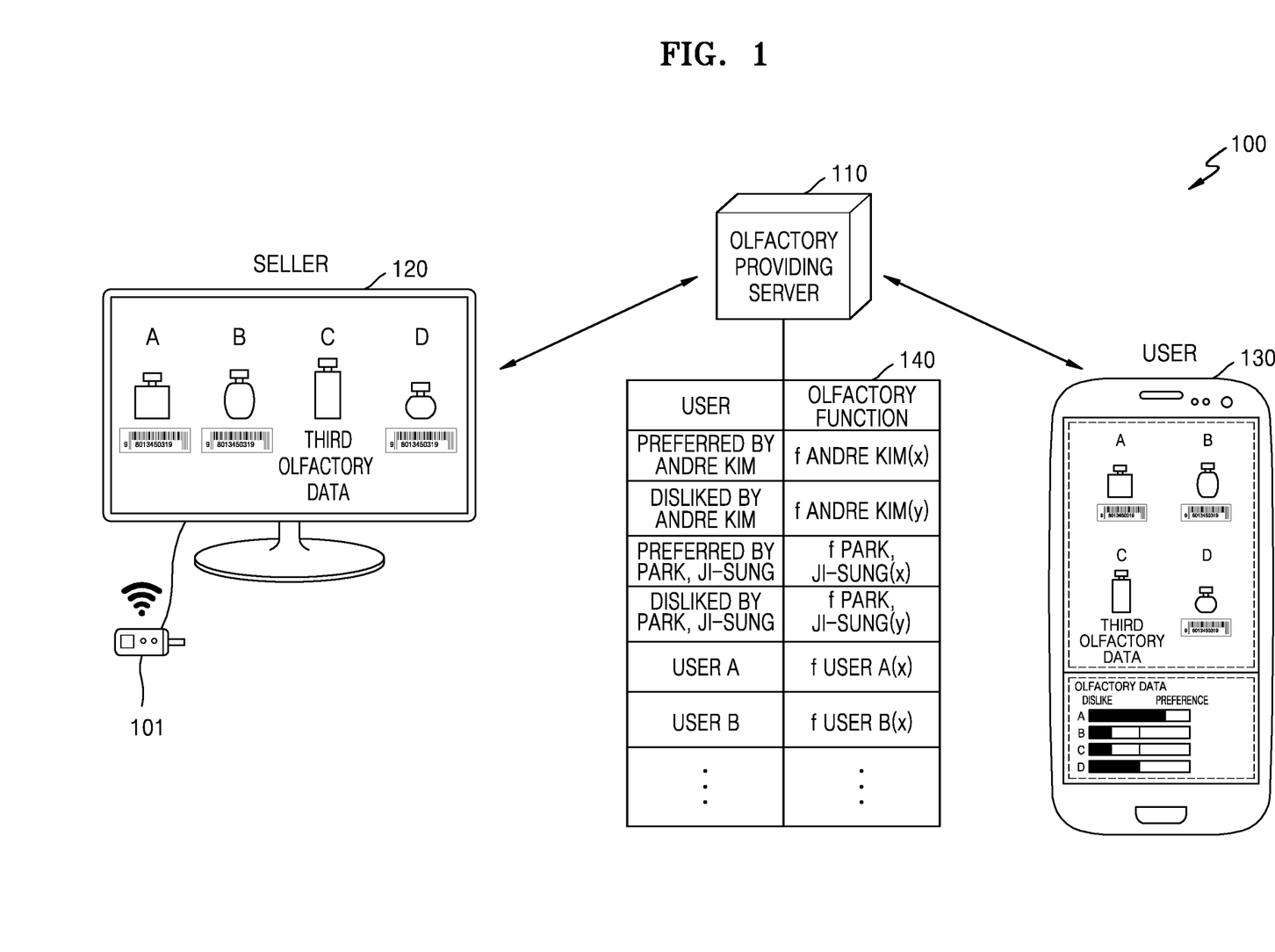
FIG. 1 is a diagram showing an olfactory data sharing system including a terminal for sharing olfactory data, according to one or more embodiments.

FIG. 1 is a diagram showing an olfactory data sharing system in which a terminal for sharing olfactory data is implemented, according to one or more embodiments.

According to an example embodiment, an olfactory data sharing system 100 may include a first terminal 120 and a second terminal 130. According to an example embodiment, the first terminal 120 and the second terminal 130 may include olfactory sensors 101 of the same type. The first terminal 120 may communicate with the olfactory sensor (not shown) in a wired/wireless fashion and provide olfactory data sensed by the olfactory sensor. The second terminal 130 may communicate with the olfactory sensor (not shown) in a wired/wireless fashion, receive the olfactory data provided from the first terminal 120, and display a user's preference regarding the received olfactory data. Also, the second terminal 130 may be implemented to receive olfactory data and preference information of a user of the second terminal 130 regarding the olfactory data from the first terminal 120. In this case, it is assumed that information regarding user olfactory function $f_{user}(x)$ is stored in the first terminal 130 in advance.

According to an example embodiment, the olfactory sensor 101 may include a plurality of sensors. For example, the olfactory sensor 101 may comprise an electrical sensor, to which an inorganic oxide is applied in the form of a thin film, micro particles, or nano particles. Also, the inorganic oxide may also be applied to the electrical sensor in the form of protein or a polymer. The olfactory sensor 101 may also be formed by culturing olfactory sensing cells extracted from various living organisms and applying the olfactory sensing cells to an electrical sensor. In this case, the electric sensor may use a transistor having a two-electrode structure or a three-electrode structure. Also, the olfactory sensor 101 may further include a gas sensor for detecting a gas, a temperature sensor for detecting a temperature, and a humidity sensor for detecting humidity.

According to an example embodiment, the olfactory sensor 101 may include an electronic nose-type sensor. An electronic nose typically uses six to twenty-four sensors to detect different odors. An electronic nose with six sensors detects and classifies odors into six odor groups, and an electronic nose with 24 sensors detects and classifies odors into 24 odor groups. For example, sensors react to different chemicals, such as hydrocarbons, alcohols, and ammonia, respectively. A pH sensor measures acidity with an electrode whose potential varies depending on the concentration of hydrogen ions (H+). When odors detected by such sensors are combined, a certain type of graph appears for each food, which acts like an odor fingerprint for a particular food.

For example, olfactory data of Pieces of Tofu, which are manufactured one day ago and stored at 5° C. and 15° C., sensed by using an electronic nose using six sensors is analyzed. After olfactory data of Pieces of Tofu, which are manufactured one day ago and stored at 5° C. and 15° C., include different hydrocarbon, alcohol, and ammonia content information. In this case, resistance ratio values obtained from the six sensors used by the electronic nose show unique patterns.

According to an example embodiment, the olfactory data sharing system 100 may further include an olfactory data providing server 110 capable of communicating with the first terminal 120 and the second terminal 130 via wires or wirelessly. The first and second terminals 120 and 130 may include a mobile phone, a smart phone, a laptop computer, a personal computer (PC), a handheld terminal, a wearable terminal, a robot, a television (TV), a tablet, a smart watch, etc., and may also include all kinds of terminals capable of communicating with an olfactory sensor in a wired/wireless fashion and including a processor capable of receiving olfactory data and machine-training and processing a user's preferences.

According to another embodiment of the disclosure, the first terminal 120 may include a perfume seller's terminal, and the second terminal 130 may include a terminal of a purchaser who wants to purchase perfume. Referring to FIG. 1, the perfume seller with the first terminal 120 provides olfactory data 122 about perfume which the perfume seller sells. Then, on the second terminal 130, preference information regarding olfactory data provided by the perfume seller is displayed. Also, the perfume seller 120 may provide the olfactory data 122 together with an image 121 of a perfume. In this case, a user's preference regarding olfactory data may be displayed along with the shape of the perfume in a purchaser's terminal.

The perfume seller 120 may describe a perfume as 'soft lavender scent and freshness of bergamot softly surrounded by sandalwood and musk' along with a video 120 of the perfume that he sells and display ingredients constituting the perfume as follows.

Top Notes: Sheer Lavender, Bergamot

Mid Notes: Star Rose, White Jasmine, Violet, Ylang Ylang, Lily of the Valley

Dry Notes: Sandalwood, Vetiver, Oakmoss, Vanilla, Amber, Soft Musk

Figure 4:
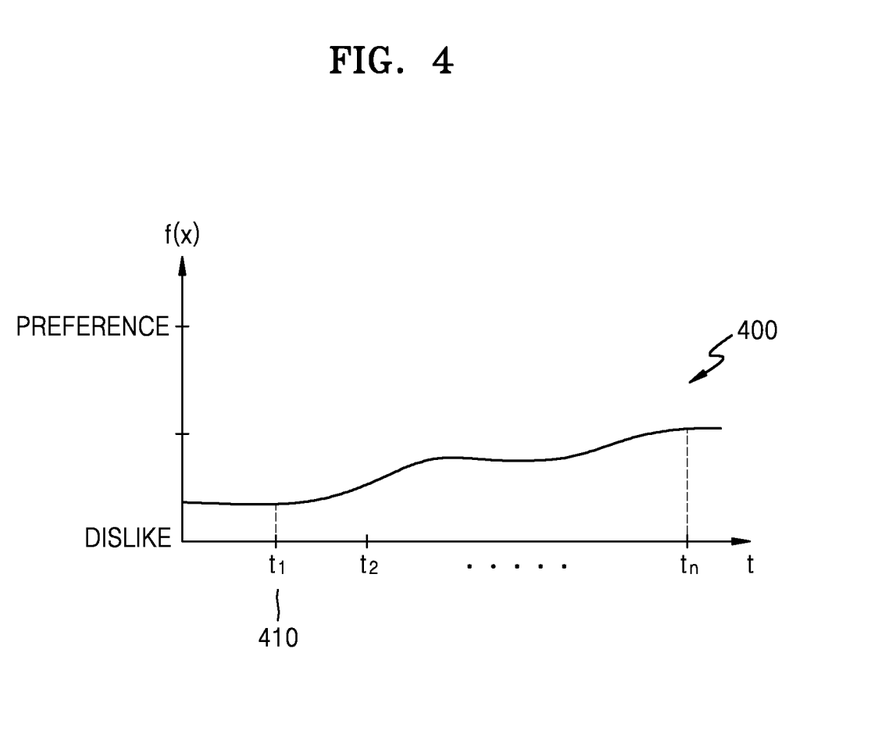
FIGS. 4 and 5 are diagrams showing an example of displaying a user preference according to the lapse of time in a terminal that received olfactory data according to one or more embodiments.
Figure 5:
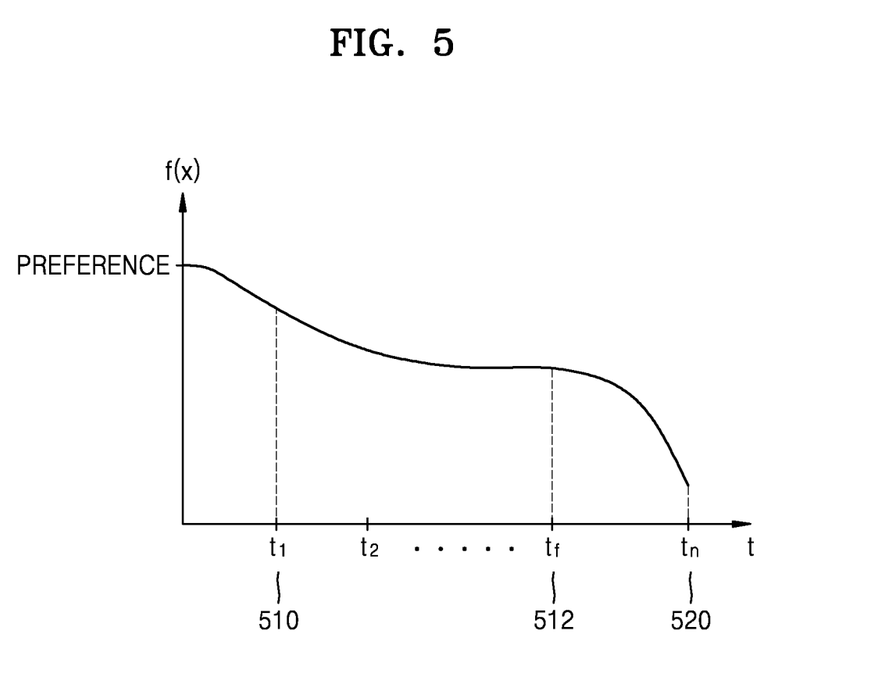

The perfume seller 120 provides olfactory data obtained by sensing the perfume by using the olfactory sensor 101 in addition to the ingredients constituting the perfume. The olfactory data may be transmitted in various forms, such as electrical signals, barcodes, and QR codes. In this case, a user's preference regarding the perfume A may be displayed on the second terminal 130 of the purchaser. As shown in the first terminal 130 of a purchaser of FIG. 1, user preferences for a perfume may indicate a degree of preference or user preferences according to the lapse of time as shown in FIGS. 4 and 5.

Figure 2:
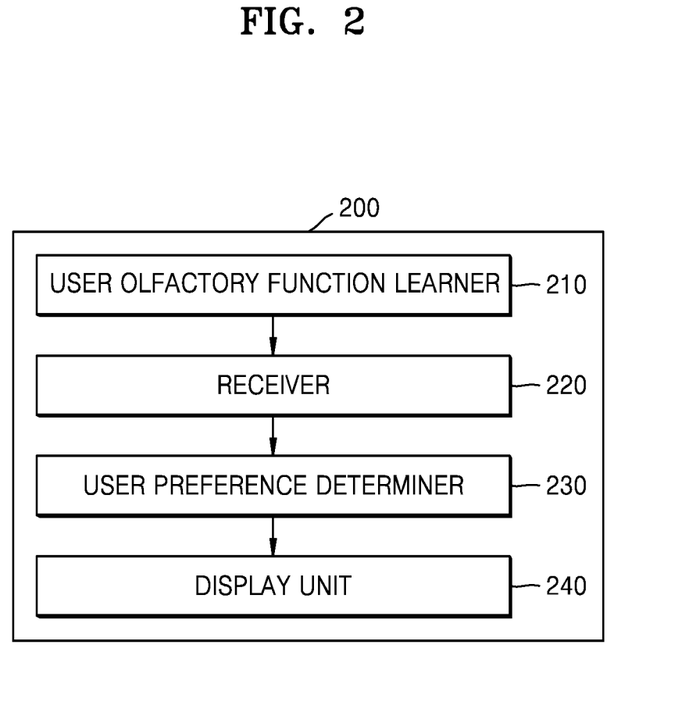
FIGS. 2 and 6 are diagrams showing internal configurations of an olfactory data sharing terminal according to one or more embodiments.
Figure 3:
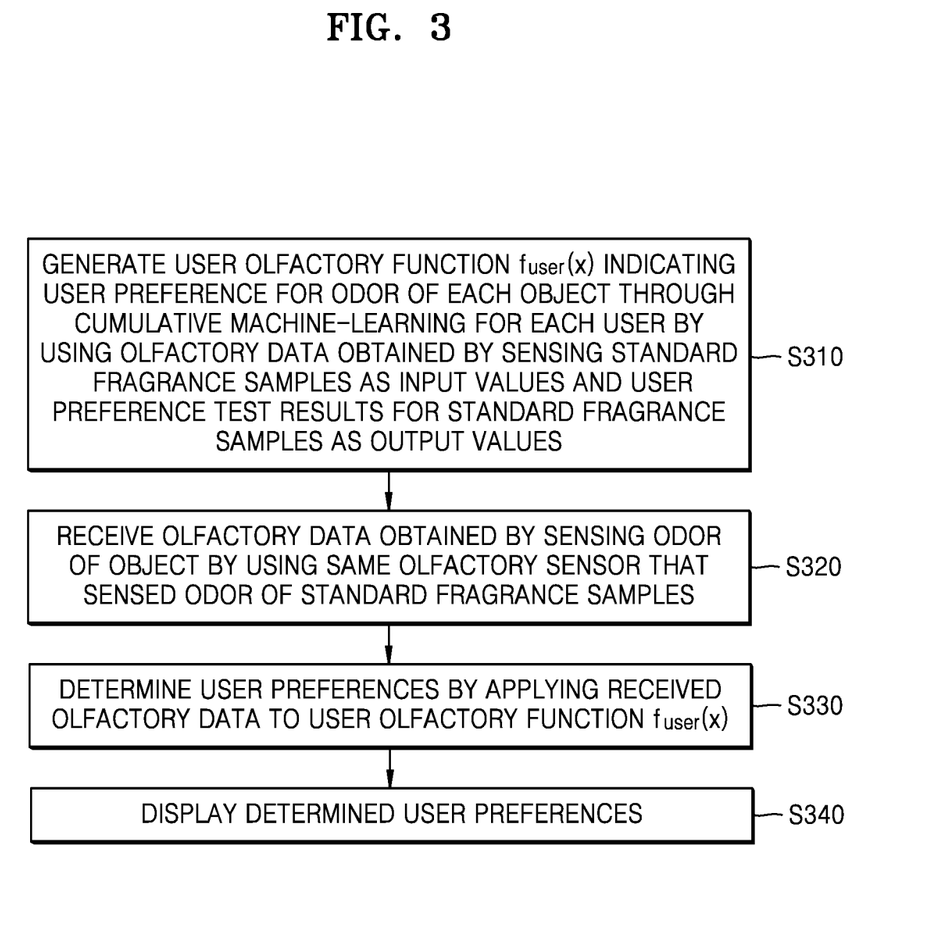
FIG. 3 is a flowchart showing determination of a preference in a terminal that receives olfactory data according to one or more embodiments.
Figure 6:
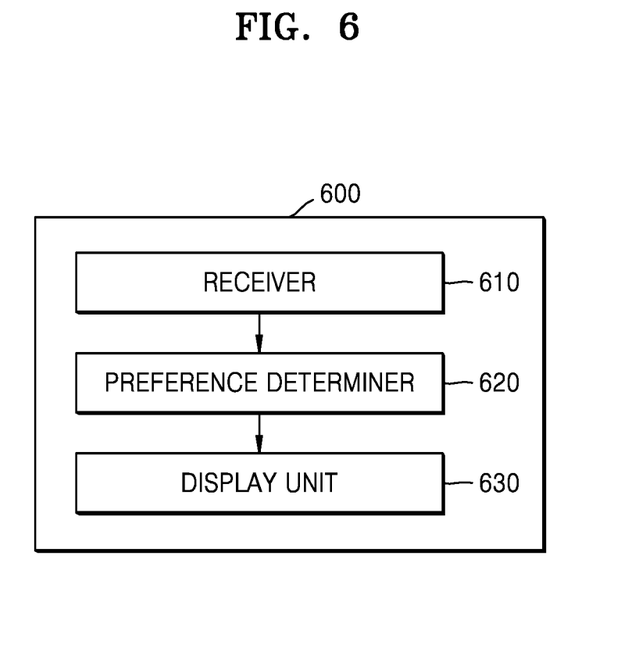

According to an example embodiment, FIGS. 2 and 3 show examples in which user preferences for olfactory data are displayed by sharing olfactory data through the olfactory data sharing terminal 200. FIG. 6 is a diagram showing an olfactory data sharing terminal 600 according to another embodiment.

According to an example embodiment, the olfactory data sharing terminal 200 includes a user olfactory function learner 210, a receiver 220, a user preference determiner 230, and a display unit 240.

The user olfactory function learner 210 generates a user olfactory function $f_{user}(x)$ indicating user preference for the odor of each object through cumulative machine-learning for each user by using olfactory data obtained by sensing standard fragrance samples as input values and user preference test results for the standard fragrance samples as output values.

FIG. 2 shows an example in which the user olfactory function learner 210 is included in the olfactory data sharing terminal 200 according to an example embodiment, and FIG. 6 shows an example in which the olfactory data sharing terminal 200 does not include the user olfactory function learner 210. In FIG. 2 and FIG. 6, corresponding components play substantially corresponding roles, and thus components will be described below with reference to FIG. 2.

A user may generate a user olfactory function $f_{user}(x)$ by using an olfactory sensor that is provided in his/her terminal or capable of communicating with his/her terminal via a wire or wirelessly. In the latter example, a user may generate his/her own olfactory function $f_{user}(x)$ in an organization where an olfactory sensor is pre-installed and store only the $f_{user}(x)$ value in his/her terminal or an olfactory data providing server (110 of FIG. 1) and use the $f_{user}(x)$ value.

In the current specification, a user's preference is used as the same meaning as a 'result value of an olfactory function $f_{user}(x)$'. In the olfactory function $f_{user}(x)$, x means an object. The user's preference may have been trained in advance through machine-training. The user may perform a process of sensing olfactory data about standard samples composed of various fragrances or incenses through an olfactory sensor and recording test results for his/her preferences for the sensed olfactory data. The machine-training may be performed by using physical signal values sensed by the olfactory sensor as input values and test result values for a user's preferences for objects sensed by the olfactory sensor as output values.

A user may perform a user preference test on the rose fragrance through standard perfume samples classified into Bulgarian roses, French roses, etc. A user preference test result is based on an individual's sense of smell, such as a preferred fragrance and a dislike fragrance. Also, a machine-learning may be performed based on physical objects, such as a preferred French rose fragrance or lily fragrance. A user may also use preferred blends as inputs for machine learning. For example, a user may input a combination of "Star Rose, White Jasmine, Violet, and Ylang Ylang" as the Mid Notes of a perfume to machine-learn the user's olfactory function $f_{user}(x)$. As a machine-training method, a deep neural network method may be used, and also, other various methods may be used.

According to an embodiment of the disclosure, the olfactory function $f_{user}(x)$ may also be expressed in the form of $f_{user}(x_1, x_2, x_3, \ldots x_n)$, and in this case, $x_1, x_2, x_3, \ldots x_n$ may represent respective variables that are sensed when an odor of an arbitrary object is sensed by the olfactory sensor or respective incenses or chemical ingredients. The variables may also include a pressure change, a temperature, gas chromatography information, information regarding chemical component constituting the object, and information regarding adsorption and desorption between odor molecules and polymer elements that are detected when sensing the odor of the object.

According to an embodiment of the disclosure, referring to FIG. 1, when olfactory data about an unknown object x is input to the olfactory function $f_{user}(x)$ that is used by the second terminal 130 or the olfactory data providing server 110, a preference determiner of the second terminal 130 or the olfactory data providing server 110 may match the olfactory data about the unknown object x with a olfactory data value sensed from a pre-stored standard sample that is most similar to the olfactory data about the unknown object x, and provide the user's predicted preference information about the unknown object x.

According to an example embodiment, the user olfactory function learner 210 may generate the user olfactory function $f_{user}(x)$ by maching-learning at least one of information regarding protein components, chemical compositions, a composition ratio, and adsorption and desorption between odor molecules and polymer elements constituting the odor of an object preferred by each user. Also, the user olfactory function learner 210 may generate the user olfactory function $f_{user}(x)$ by machine-learning at least one of gas chromatography information for analyzing gas ingredients generated from an odor of an object, information regarding chemical ingredients constituting the object, and information regarding absorption and desorption between odor molecules and polymer elements, which may be extracted from the olfactory data, and sensing information sensed by each of a plurality of sensors constituting the olfactory sensor (operation S310).

The receiver 220 receives the olfactory data (operation S320). In this case, the transmitter (not shown) assumes that the olfactory data is sensed by using the same olfactory sensor as the olfactory sensor used when the receiver 220 generated the user olfactory function $f_{user}(x)$. The user preference determiner 230 determines a user's preference by inputting the olfactory data sensed by the receiver 220 as an x value to the user olfactory function $f_{user}(x)$.

In this case, a user's preference may be shown in the form of a comprehensive score of preference or dislike as in the example displayed on the second terminal 130 of the purchaser of FIG. 1 or may be displayed on the display unit 240 in the form of preference according to the lapse of time as in the embodiment shown in FIG. 4 or 5 (operation S340). Perfume has different retention periods of odor molecules depending on information regarding the adsorption and desorption between the odor molecules constituting fragrances and polymer elements present in the air, gas ingredients constituting the odor molecules, and various other factors, and thus a user may show different preferences according to the lapse of time.

Referring to FIG. 4, a display unit (240 of FIG. 2) may display a user's preference regarding the olfactory data in time series 400. In this case, a prediction time t1 in which the top note ingredients of the perfume detected from the olfactory data are retained, a user's preference for the top note ingredients, a time tn in which the top note ingredients disappear and the middle note ingredient are retained, the user's preference for the middle note ingredients, a time in which, after the time tn, the middle note ingredients disappear and the dry note ingredients remain, and the user's preference for the dry note ingredients may be displayed. FIG. 5 also shows an example in which a user's preference for the olfactory data is displayed in time series 510, 512, and 520 on a display unit (240 of FIG. 2).

Figure 7:
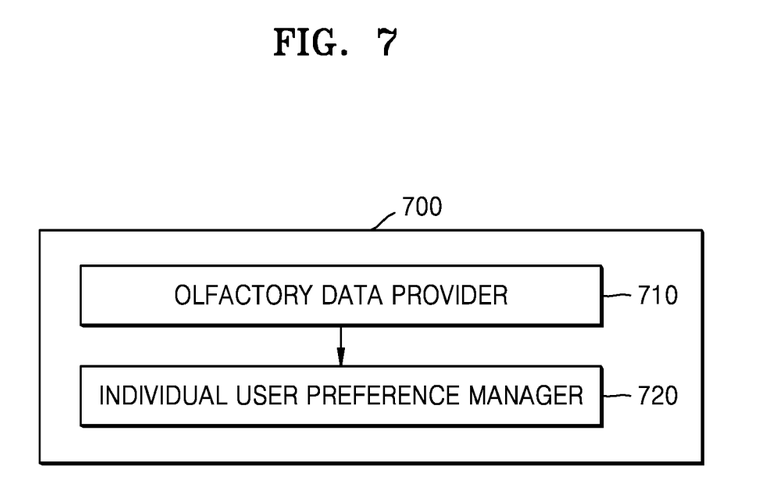
FIG. 7 is a diagram showing an internal configuration of an olfactory data sharing terminal according to one or more embodiments.

FIG. 7 is a diagram showing an internal configuration of an olfactory data sharing terminal 700 according to another embodiment.

The olfactory data sharing terminal 700 may include a case in which the first terminal 120 of FIG. 1 communicates with the olfactory data providing server 110 in a wired/wireless fashion or self-implements a function of the olfactory data providing server 110.

The olfactory data sharing terminal 700 includes an olfactory data provider 710 and an individual user preference manager 720. The olfactory data provider 710 may provide olfactory data obtained by sensing an odor of an object through an olfactory sensor.

The user preference manager 720 may have stored an olfactory function $f_{user}(x)$ for each user in advance, and manage a user preference for olfactory data for each user based on the olfactory function $f_{user}(x)$ stored in advance for each user. An example of the user preference manager 720 may be an olfactory data table 140 of FIG. 1.

The olfactory data sharing terminal 700 may predict pre-stored users' preferences for olfactory data obtained by sensing an odor of an arbitrary object, based on the olfactory function $f_{user}(x)$ for each user stored in advance in the user preference manager 720. Also, the olfactory data sharing terminal 700 may recommend perfume manufactured to have kinds of olfactory sensation preferred by each user, based on the user preference information stored in the user preference manager 720, or may sell the user preference information stored in the user preference manager 720 to a subcontractor or a perfume manufacturer.

The terminal described above may be implemented with a hardware component, a software component, and/or a combination of a hardware component and a software component. For example, the terminal and components described in the embodiments may be implemented by using one or more general-purpose computers or a special-purpose computer, such as, for example, a processor, a controller, an arithmetic logic unit (ALU), a digital signal processor, a microcomputer, a field programmable gate array (FPGA), a programmable logic unit (PLU), a microprocessor, or another terminal capable of executing and responding to instructions. A processor may execute operating system (OS) and one or more software applications that are executed on the OS. Also, the processor may access, store, control, process, and create data in response to execution of software.

According to one or more embodiments, an olfactory data sharing terminal may enable a user to indirectly recognize his/her preferred olfactory sensation online based on olfactory data of an object, without actually recognizing an olfactory sensation of the object.

According to one or more embodiments, in case of purchasing cosmetics or perfume, information indicating whether fragrances thereof are fragrances preferred by a user may be provided by using an olfactory data sharing system, and thus accurate information may be provided to the user for selecting a product without smelling the fragrances.

According to one or more embodiments, an olfactory data sharing system may collect a user's olfactory function in advance to predict the user's preferences and to suggest products with olfactory data preferred by the user to the user.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of sharing olfactory data between the real world and the online world, the method performed by a terminal having an olfactory sensor and a display unit, the method comprising:
    generating a user olfactory function $f_{user}(x)$ through cumulative machine-learning for a user by using sample olfactory data obtained by sensing standard fragrance samples by the sensor as input values and user preference test results for the standard fragrance samples as output values so that the user olfactory function fuser(x) indicates a user preference for an odor of each of the standard fragrance samples;
    receiving olfactory data obtained by sensing an odor of an object by using the olfactory sensor;
    determining a user preference for the odor of the object by applying the received olfactory data to the user olfactory function $f_{user}(x)$; and
    displaying the determined user preference for the odor of the object on the display unit.

2. The method of claim 1,
    wherein the received olfactory data includes at least one of gas chromatography information for analyzing gas ingredients generated from an odor of an object, information regarding chemical ingredients constituting the object, information regarding absorption and desorption between odor molecules and polymer elements, which may be extracted from the olfactory data, and sensing information sensed by each of a plurality of sensors constituting the olfactory sensor.

3. The method of claim 1,
    wherein the user olfactory function $f_{user}(x)$ is generated by machine-learning with respect to at least one of information regarding protein components, chemical compositions, a composition ratio, and adsorption and desorption between odor molecules and polymer elements constituting the odor of an object preferred by the user.

4. The method of claim 1, wherein the determining of the user preference matches the received olfactory data with an olfactory data value of the sample olfactory data that is most similar to the olfactory data, and the olfactory data value is input as an x value in the olfactory function $f_{user}(x)$ to determine the user preference.

5. The method of claim 1, wherein the determining of the user preference determines the user preference for the odor of the object according to the received olfactory data that changes over time based on a result value of the olfactory function fuser(x).

6. The method of claim 1, wherein the display unit displays the user preference with respect to the odor of the object according to the lapse of time.

7. An olfactory data sharing system for recognizing an olfactory preference, the olfactory data sharing system comprising:
    a first terminal configured to generate a user olfactory function $f_{user}(x)$ through cumulative machine-learning for each of a plurality of users by using sample olfactory data obtained by sensing standard fragrance samples as input values and user preference test results for the standard fragrance samples as output values so that the user olfactory function fuser(x) indicates a user preference for an odor of each of the standard fragrance samples; and
    a second terminal configured to
        receive, from the first terminal, the sample olfactory data and the generated user olfactory function $f_{user}(x)$,
        receive olfactory data of an object by sensing an odor of the object using an olfactory sensor,
        determine a user preference for the odor of the object by applying the received olfactory data to the received user olfactory function $f_{user}(x)$, and
        display the determined user preference for the odor of the object on a display unit of the second terminal,
    wherein the second terminal determines the user preference for the odor of the object according to the received olfactory data that changes over time based on a result value of the olfactory function fuser(x), and displays the user preference with respect to the odor of the object according to the lapse of time.

8. The olfactory data sharing system of claim 7, further comprising
    a user preference manager configured to receive, from the first terminal, the sample olfactory data and the olfactory function $f_{user}(x)$ for the each of the plurality of users, and generate each user preference for the sample olfactory data for each user based on the olfactory function $f_{user}(x)$.

9. The olfactory data sharing system of claim 8, wherein the first terminal is further configured to
    predict a user preference for olfactory data obtained by sensing an odor of an arbitrary object, based on the olfactory function $f_{user}(x)$ for each user stored in the user preference manager.

10. An olfactory data sharing terminal comprising:
    an olfactory data provider configured to provide olfactory data obtained by sensing an odor of an object through an olfactory sensor; and
    a user preference manager configured to store an olfactory function fuser(x) for each of a plurality of users, and manage a user preference for the olfactory data for each user based on the olfactory function fuser(x) stored for each user,
    wherein a user olfactory function $f_{user}(x)$ is generated through cumulative machine-learning for each of the plurality of users by using sample olfactory data obtained by sensing standard fragrance samples by the sensor as input values and user preference test results for the standard fragrance samples as output values so that the user olfactory function fuser(x) indicates a user preference for an odor of each of the standard fragrance samples.

11. An olfactory data sharing terminal comprising:
    an olfactory sensor configured to generate olfactory data obtained by sensing an odor of an object;
    a user olfactory function learner configured to generate a user olfactory function $f_{user}(x)$ through cumulative machine-learning for each of a plurality of users by using sample olfactory data obtained by sensing standard fragrance samples as input values and user preference test results for the standard fragrance samples as output values so that the user olfactory function fuser(x) indicates a user preference for an odor of each of the standard fragrance samples;
    a receiver configured to receive olfactory data obtained by sensing an odor of an object by using the olfactory sensor;
    a user preference determiner configured to determine a user preference for the odor of the object by applying the received olfactory data to the user olfactory function $f_{user}(x)$; and
    a display unit configured to display the determined user preference for the odor of the object on the display unit.

* * * * *